United States Patent

Koyama et al.

[11] Patent Number: 5,556,516
[45] Date of Patent: Sep. 17, 1996

[54] METHOD FOR THE PURIFICATION OF 1-AMINOPROPANEDIOL-2,3

[75] Inventors: Hiroshi Koyama; Etsuo Takemoto, both of Hiroshima, Japan

[73] Assignee: Daicel Chemical Industries, Ltd., Osaka-fu, Japan

[21] Appl. No.: 411,208

[22] Filed: Mar. 27, 1995

Related U.S. Application Data

[62] Division of Ser. No. 20,437, Feb. 22, 1993, which is a continuation of Ser. No. 739,068, Aug. 1, 1991, abandoned.

[30] Foreign Application Priority Data

Aug. 1, 1990 [JP] Japan ..................................... 2-204395
Jul. 8, 1991 [JP] Japan ..................................... 3-166603

[51] Int. Cl.$^6$ ..................................... B01D 3/10
[52] U.S. Cl. ..................... 203/91; 159/49; 159/DIG. 16; 202/158; 203/89; 203/99; 564/507
[58] Field of Search .................................. 203/89, 91, 99, 203/DIG. 6; 564/475, 474, 495, 507, 497; 202/158; 159/62, 49, DIG. 10, DIG. 16

[56] References Cited

U.S. PATENT DOCUMENTS

| 2,226,534 | 4/1937 | Lichty. | |
|---|---|---|---|
| 4,356,323 | 10/1982 | Kleemann et al.. | |
| 4,358,615 | 11/1982 | Kleemann et al.. | |
| 4,360,697 | 11/1982 | Kleemann et al.. | |
| 4,503,252 | 3/1985 | Felder et al. ........................... | 564/474 |
| 5,023,379 | 6/1991 | Felder et al.. | |
| 5,053,545 | 10/1991 | Marman et al. ........................ | 564/495 |

FOREIGN PATENT DOCUMENTS 0075929 4/1983 European Pat. Off..

*Primary Examiner*—Virginia Manoharan
*Attorney, Agent, or Firm*—Sughrue, Mion, Zinn, Macpeak & Seas

[57] ABSTRACT

1-aminopropanediol-2,3 containing 2-aminopropanediol-1,3 of less than 0.30% by weight can be prepared by the present purification process, which involves distilling a 1-aminopropanediol-2,3 containing at least 0.3% of 2-aminopropanediol-1,3 based on the weight of 1-aminopropanediol-2,3 using a distillation column, said distillation column having low pressure loss.

12 Claims, 1 Drawing Sheet

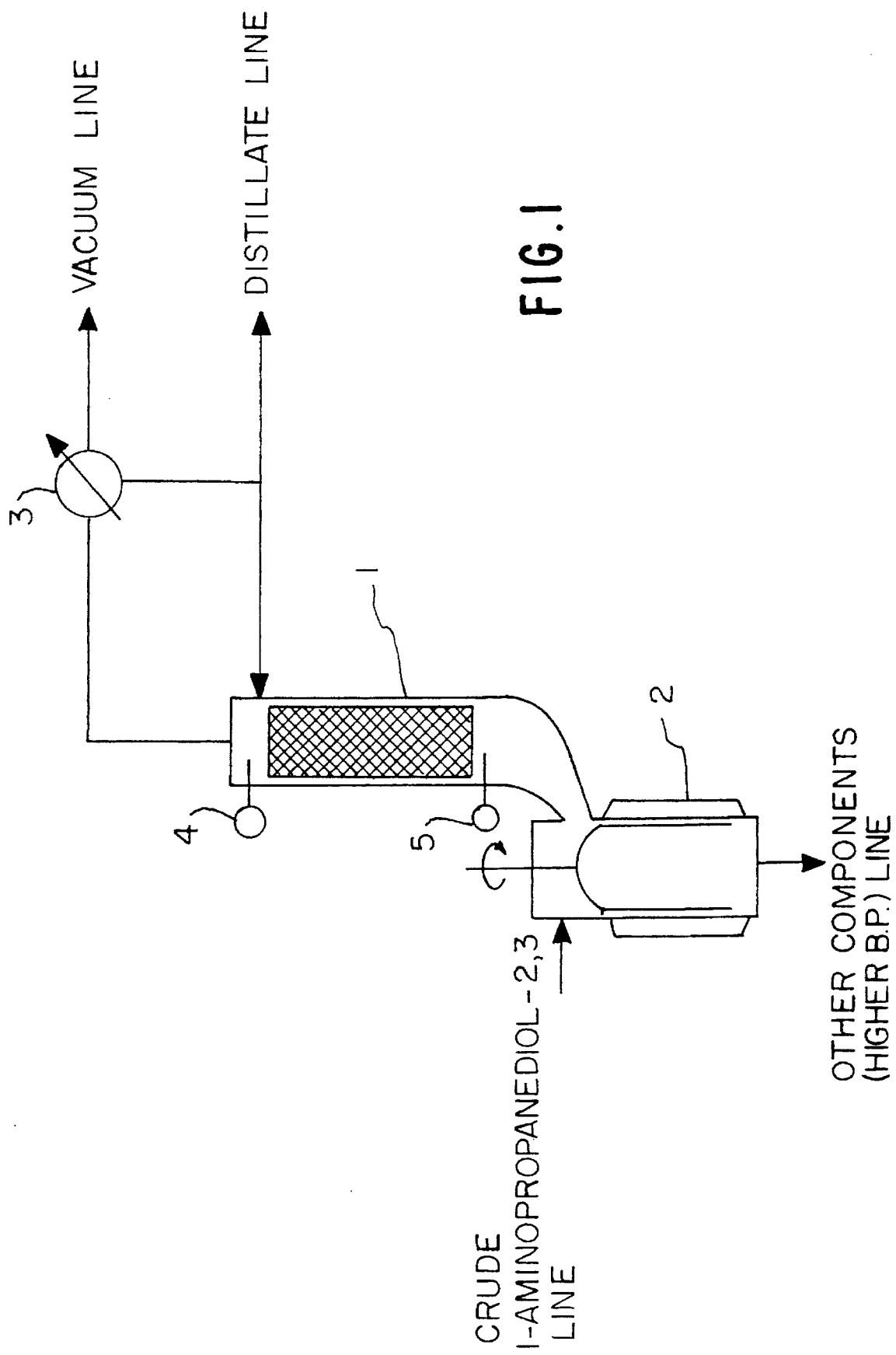

METHOD FOR THE PURIFICATION OF 1-AMINOPROPANEDIOL-2,3

This is a divisional of application Ser. No. 08/020,437, filed Feb. 22, 1993, which was a continuation application of application Ser. No. 07/739,068 filed Aug. 1, 1991, now abandoned.

FIELD OF THE INVENTION

The present invention relates to a highly purified 1-aminopropanediol-2,3 and a method for the purification thereof.

In more detail, the present invention relates to a highly purified 1-aminopropanediol-2,3 containing a reduced amount of 2-aminopropanediol-1,3 which is a by-product and an undesired compound for a use, and a method for the purification thereof.

BACKGROUND OF THE INVENTION 1-aminopropanediol-2,3, which is useful as a starting material for non-ionic X-ray contrast agents, is an industrially interesting product (for example, see Belgian Pat. No. 855,580), and the demand therefore recently has increased.

Hitherto, it has typically been produced by a reaction of glycidol with ammonia.

For example, a process for the preparation of 1-aminopropanediol- 2,3-which comprises a reaction of glycidol with 25% aqueous ammonia and a final distillation under reduced pressure conditions to obtain the refined product, is disclosed in "Ber. Deutsche Chem Ges" Vol 32, pages 750–757, 1899 (L. Knorr et al).

Furthermore, a process for the preparation of 1-aminopropanediol- 2,3 which comprises a reaction of glycerine-alpha-monochlorohydrin with 25% aqueous ammonia and a final distillation under reduced pressure conditions to obtain the refined product, is disclosed in "Journal of Organic Chemistry", Vol. 27, pages 2231–2233, 1962 (K. Baum et al).

Still further, Japanese Patent Examined Publication (Kokoku) No. 37,342/1990 (corresponding to U.S. Pat. No. 4,356,323), Japanese Patent Unexamined Publication (Kokai) No. 161357/1981 (corresponding to U.S. Pat. No. 4,360,697), and Japanese Patent Examined Publication (Kokoku) No. 37,343/1990 (corresponding to U.S. Pat. No. 4,358,615) teach that 1-aminopropanediol-2,3 can be effectively prepared by a reaction of glycidol with liquid ammonia under pressurized conditions.

The above described disclosures disclose only the yield of 1-aminopropanediol-2,3 and the reaction conditions, such as a molar ratio between starting materials, reaction temperatures, reaction pressures, the amount of water to be used together with liquid ammonia, etc.

However, it has been known that 2-aminopropanediol-1,3, which is an undesirable impure component, and which can not be reduced to less than 0.30% by weight by the prior techniques without an improvement, is by-produced, even though in a minor amount, in the preparation of 1-aminopropanediol-2,3.

Heretofore, commercially supplied 1-aminopropanediol-2,3 has contained from more than 0.30 to 0.50% or more (based on the weight of 1-aminopropanediol-2,3) of 2-aminopropanediol-1,3.

It is noted that 2-aminopropanediol-1,3 adversely affects the use described above, even though it is present in a relatively minor amount.

More specifically, for example, there has been a problem such as low yields of final product in the case that the non-ionic X-ray contrast agents are manufactured using 1-aminopropanediol-2,3 containing large amounts of 2-aminopropanediol-1,3.

Accordingly, it has been desired that 1-aminopropanediol-2,3 containing small amounts of 2-aminopropanediol-1,3 would be developed.

As the result of the background described above, the present inventors have earnestly investigated to prepare a highly purified 1-aminopropanediol-2,3 containing small amounts of 2-aminopropanediol-1,3, which can be obtained by distilling with a distillation column having low pressure loss from a crude 1-aminopropanediol-2,3 containing more than 0.30% of 2-aminopropanediol-1,3 (based on the weight of 1-aminopropanediol-2,3).

SUMMARY OF THE INVENTION

It is an object of the present invention to provide a highly purified 1-aminopropanediol-2,3.

It is another object of the present invention to provide a method for the purification thereof.

More specifically, in accordance with the present invention, there is provided 1-aminopropanediol-2,3 containing 2-aminopropanediol-1,3 in amount of less than 0.30% by weight.

In another aspect, the present invention is directed to a method for the preparation of said highly purified 1-aminopropanediol-2,3.

BRIEF DESCRIPTION OF THE DRAWING

FIG. 1 illustrates a preferred embodiment in order to carry out the present invention, by a schematic representation.

DETAILED DESCRIPTION OF THE INVENTION

The highly purified 1-aminopropanediol-2,3 and the purification method thereof according to the present invention are described hereinafter in more detail.

The content of 2-aminopropanediol-1,3 in the present invention is calculated by the following equation.

$$C_{2\text{-}APD} = \frac{P_{2\text{-}APD} \times 100}{P_{1\text{-}APD}}$$

In the equation, $C_{2\text{-}APD}$ is the concentration of 2-aminopropanediol- 1,3, and $P_{1\text{-}APD}$ and $P_{2\text{-}APD}$ are defined as a peak area in relation to 1-aminopropanediol-2,3 and 2-aminopropanediol- 1,3, respectively, obtained in a gas chromatographic analysis after 1-aminopropanediol-2,3 is acetylated by an acetylation agent, such as trifluoroacetic anhydride.

The gas chromatographic analysis is preferably carried out with the following measurement conditions.

| | |
|---|---|
| Column Packing | ULBON NR-1701 (Fused silica capillary) |
| Column | Length 25 m, Internal Diameter 0.2 mm, Film Thickness 0.25 microns |
| Column Temperature | Initial 140° C. Final 220° C. Rate 5° C./minute |
| Detector | Flame Ionization |

| | |
|---|---|
| Injection Temperature | 250° C. |
| Detector Temperature | 250° C. |
| Carrier Gas | Helium |
| Flow Rate | 1.14 ml/minute |
| Split Value | 1:65.14 |
| Sample | 1-aminopropanediol-2,3 Derivative Sample treated by Trifluoroacetic anhydride |
| Sample Size | 1.0 micro liter |
| Range | 10 |
| Calculation | Area Percent |

1-aminopropanediol-2,3 is prepared by the reaction of glycidol with ammonia according to the reaction scheme as described below.

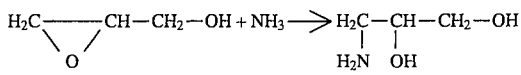

In the reaction, a certain amount of 2-amino-propanediol-1,3 is unavoidably by-produced, which is represented by the following formula.

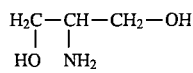

In the case of the preparation of 1-aminopropanediol-2,3 from glycerine-alpha-monochlorohydrin and ammonia, it appears that glycidol is also generated as an intermediate according to the reaction scheme as described below.

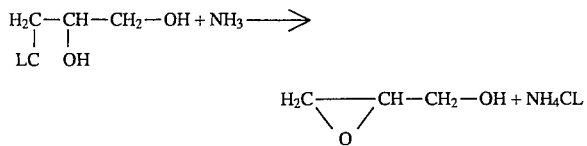

Accordingly, a certain amount of 2-aminopropanediol-1,3 is unavoidably by-produced in this case also, from the same viewpoint.

As a result, both the reaction of glycidol with ammonia and the reaction of glycerine-alpha-monochlorohydrin with ammonia by-produce 2-aminopropanediol-2,3 unavoidably not less than 0.30% (based on the weight of 1-aminopropanediol- 2,3) in the reaction processes of 1-aminopropanediol-2,3.

Furthermore, 1-aminopropanediol-2,3 and 2-aminopropanediol- 1,3 are very similar in their chemical structures; as a result, they are very close in their boiling points. Accordingly, it has been believed that 2-aminopropanediol-1,3 can not be sufficiently removed from 1-aminopropanediol- 2,3 by conventional distillation processes.

As described hereinabove, the commercially supplied conventional 1-aminopropanediol-2,3 has unavoidably contained 2-aminopropanediol-1,3 of from more than 0.30 to 0.50% by weight or more.

The starting materials and the purification methods thereof according to the present invention will be described hereinafter.

The starting material to be used in the present invention is a crude 1-aminopropanediol-2,3 containing 2-aminopropanediol- 1,3 of more than 0.30% (based on the weight of 1-aminopropanediol-2,3), which can be readily prepared by the processes disclosed in the prior arts as described hereinabove.

In other words, the conventional reactions of ammonia with glycidol or glycerine-alpha-monochlorohydrin inevitably give the starting crude 1-aminopropanediol-2,3 containing 2-aminopropanediol-1,3 in an amount of more than 0.30% (based on the weight of 1-aminopropanediol-2,3).

Ammonia, which is one of the starting materials, can be used as liquid ammonia or an aqueous ammonia.

As described hereinabove, Japanese Patent Examined Publication (Kokoku) No. 37,342/1990 (corresponding to U.S. Pat. No. 4,356,323), Japanese Patent Unexamined Publication (Kokai) No. 161357/1981 (corresponding to U.S. Pat. No. 4,360,697), and the Japanese Patent Examined Publication (Kokoku) No., 37,343/1990 (corresponding to U.S. Pat. 4,358,615) teach the uses of liquid ammonia.

The crude 1-aminopropanediol-2,3 obtained by the processes described in such earlier disclosures can be also used as a material for treatment according to the present invention.

Furthermore, commercially supplied purified conventional 1-aminopropanediol-2,3 containing 2-aminopropanediol- 1,3 in an amount of from more than 0.30% to 0.50% by weight or more as an impurity (based on the weight of 1-aminopropanediol- 2,3), can also be used as a material for treatment in accordance with the present invention.

A specific method for the preparation of 1-amino-propanediol- 2,3 containing 2-aminopropanediol-1,3 of less than 0.30% by weight, preferably, of not more than 0.25% by weight, more preferably, of not more than 0.20% by weight, which comprises a distillation of a crude 1-aminopropanediol- 2,3 containing more than 0.30% of 2-aminopropanediol- 1,3 with a distillation column having low pressure loss, is described in further detail hereinafter.

The present invention is characterized in that a crude 1-aminopropanediol-2,3 is distilled with a distillation column having a low pressure loss or a distillation column having pressure loss of not more than 0.5 Torr per one theoretical plate, at a temperature range under which 1-aminopropanediol- 2,3 does not color, so that the content of 2-aminopropanediol-1,3 is reduced.

The phrase "a distillation column having low pressure loss" described herein means that the pressure loss per one theoretical plate is low, and does not refer to "a pressure loss per a specified height", such as, for example, one meter.

As described hereinabove, 1-aminopropanediol-2,3 which is the desired product, and 2-aminopropanediol-1,3 which is an impure component, are very close in their boiling points caused by their closely similar chemical structures.

However, as a result of investigation by the present inventors, it has been found that the boiling point of 2-aminopropanediol- 1,3 is slightly higher than the boiling point of 1-aminopropanediol-2,3.

The present invention is based on taking advantage of the presence of the difference between their boiling points, even though it is very slight.

It appears that it is possible to separate 1-aminopropanediol- 2,3 from 2-aminopropanediol-1,3 by distillation, because there is a difference in their boiling points.

However, the difference in their boiling points is very slight, so it is a truism that many more theoretical plates are required for separation of 1-aminopropanediol2,3 from 2-aminopropanediol-1,3 by distillation.

Total pressure losses through the distillation column inevitably increase as the number of the theoretical plates increases, and the pressure increases at the bottom of the column.

As a result, temperatures increase at the bottom of the column.

It is noted that 1-aminopropanediol-2,3 itself and other components with higher boiling points in the crude solution are thermally unstable, and have a tendency of undergoing decomposition reactions under high temperature conditions such as more than approximately 200° C., although depending upon the period of time under heating.

It was found by our investigations that the product (1-aminopropanediol-2,3) obtained by distillation has a tendency of coloring because of the thermal decomposition reactions.

Further investigations in addition to the above investigations were carried out.

As a result, it was found that colorless purified 1-aminopropanediol- 2,3 with less than 0.30% by weight of 2-aminopropanediol- 1,3 (based on the weight of 1-aminopropanediol- 2,3) can be obtained by distillation with a distillation column in which pressure loss per one theoretical plate is not more than 0.5 Torr.

It is noted that a distillation column having "low pressure loss" in the present invention is preferably a distillation column in which the "low pressure loss per one theoretical plate" is, more specifically, not more than 0.5 Torr.

Usually, a pressure loss can readily be measured as "a pressure loss per a unit height" in the case of a distillation column.

Accordingly, it is required to determine "the number of theoretical plates per a unit height" in order to calculate "pressure loss per one theoretical plate" which is a definition in relation to pressure loss of a distillation column to be used in the present invention.

The number of theoretical plates per a unit height can be readily calculated by Fenske's equation [(Kagaku Kogaku Benran, 4th edition), page 598, 1978, published by Maruzen, Ltd. in Japan].

For example, it can be readily calculated by the data obtained from total reflux test using two components in which the relative volatility is nearly constant over a wide range of compositions, that is, it is a nearly ideal system (e.g., chlorobenzene/ethylbenzene or trans-decalin/cis-decalin, etc.).

Such distillation column having "low pressure loss per one theoretical plate" can be specifically obtained by using a typical packing described below.

The specific packing includes "Sumitomo/Sulzer Packing BX type or CY type" or "Sumitomo/Sulzer-Labopacking", "Sumitomo/Mela Packing" (supplied by Sumitomo Heavy Industries, Ltd.) and "Techno Pack 100MD or 50MS" (supplied by Mitsui & Co. Ltd.), which are supplied on a commercial basis.

All of the above described packings, which are stacked packings, have a pressure loss of not more than 0.5 Torr per one theoretical plate in a conventional range for uses thereof.

In the case of Oldershaw type plate column, from 2 to 4 actual plates usually correspond to one theoretical plate.

Furthermore, vapor inevitably passes through liquid part, whereby there is caused a pressure loss corresponding to the liquid height per one actual plate.

On the other hand, pressure losses are low in the case of a packed column, because packed columns do not cause such phenomena.

The above described packings, which are well-known and commercially available, are designed so that the pressure loss therethrough becomes low. The required number of total theoretical plates of a distillation column to be used in the present invention varies depending, for example, upon the content of 2-aminopropanediol-1,3 in the starting material, the target content of 2-aminopropanediol- 1,3 in a product, the target yield of 1-aminopropanediol- 2,3, and the reflux ratio.

The number of total theoretical plates is usually used in a range of from 3 to 100, and preferably, from 5 to 30.

The liquid temperatures and pressures in an evaporation vessel, which is attached to the bottom of the distillation column, varies depending, for example, upon the concentration of other components with higher boiling points in a crude 1-aminopropanediol-2,3, the target yield of 1-aminopropanediol-2,3, the number of the theoretical plates of the distillation column, and the pressure loss.

Specifically, the distillation is usually carried out in a temperature range of from 80° to 200° C. and a pressure range of from 0.1 to 30 Torr, in the evaporation vessel.

FIG. 1 illustrates a preferred embodiment in order to carry out the present invention, which is a schematic representation outlined.

In FIG. 1, 1 is a distillation column in which a packing having a pressure loss of not more than 0.5 Torr per 1 theoretical plate is filled, 2 is an evaporator, 3 is a condenser, 4 is a pressure gauge equipped at the top of the distillation column and 5 is a pressure gauge equipped at the bottom of the distillation column.

The evaporator 2 to be used in the present invention is not limited in type, provided that the holding time of a liquid is preferably maintained less than 1 hour in the evaporator in order to prevent coloring by thermal decomposition of 1-aminopropanediol-2,3 itself and other components with higher boiling points in the crude 1-aminopropanediol-2,3.

For example, a natural circulation evaporator, a forced circulation evaporator and a liquid-film type evaporator, which are classified in "Kagaku Kougaku Tsuron I" (edited by Haruo Hikita, the third edition, page 90, 1971, published by Asakura Shoten, in Japan), can unlimitedly be used.

Of them, a liquid-film type evaporator, in which the holding time of a liquid is short, is preferably be used.

Particularly, a wiped film evaporator is preferably used because it is capable of preventing a decrease of heat transfer efficiency even in the case of relatively highly viscous liquids, for example, 1-aminopropanediol-2,3 itself and the crude solutions thereof containing other components with higher boiling points.

The following Examples are given to illustrate the practice of this invention but they are not intended in any way to act to limit the scope of the invention.

PREPARATION EXAMPLE OF STARTING MATERIAL

A crude 1-aminopropanediol-2,3 containing not less than 0.30% (based on the weight of 1-aminopropanediol-2,3) of 2-aminopropanediol-1,3, which is a starting material in the present invention, was prepared by the following method.

A crude 1-aminopropanediol-2,3, which was obtained by the reaction of glycidol with an aqueous ammonia, was distilled off in order to remove ammonia and water under a reduced pressure to obtain the crude 1-aminopropanediol-2,3 (designated as a crude solution 1) having the following composition.

| | |
|---|---|
| 1-aminopropanediol-2,3 | 74.43% by weight |
| 2-aminopropanediol-1,3 | 0.37% by weight |
| (based on the weight of 1-aminopropanediol-2,3: 0.50% by weight) | |
| H$_2$O | 1.14% by weight |
| Other components with higher boiling points | 24.06% by weight |

EXAMPLE 1

A distillation apparatus, in which a wiped film evaporator equipped with a jacket (while maintaining heating by steam) made of a stainless steel and a vacuum jacketed distillation column filled with a stacked packing ("Sulzer Labo-Packing" supplied by Sumitomo Heavy Industries, Ltd., having a specific surface area of 1700 m$^2$/m$^3$, 50 mm in diameter× 385 mm in height) were combined, was operated while charging the crude solution 1 obtained in the above Preparation Example at a feed rate of 245.7 g/hour, under a pressure of 8 Torr at the top of the distillation column, a pressure of 12.5 Torr at the bottom of the distillation column, and a reflux ratio of 1 to distill off 1-aminopropanediol-2,3.

Steam pressure, which was supplied into the jacket of the evaporator, was adjusted so that the yield of a product was adjusted at approximately 97%.

As the result, the product was distilled off at a speed of 177.3 g/hour (the yield of the product corresponded to 97%).

The product obtained exhibited a color hue of 20 (APHA), and the 2-aminopropanediol-1,3 content of 0.20% (based on the weight of 1-aminopropanediol-2,3).

It is noted that the number of the theoretical plates of the column used in the distillation was 11.4 (calculated by Fenske's equation) based on the data obtained by total reflux test using chlorobenzene/ethylbenzene.

Accordingly, the pressure loss per one theoretical plate was 0.4 Torr [(12.5–8)/11.4=0.4].

It is noted that a falling film evaporator equipped with a jacket (heating by steam) made by a stainless steel was also used in place of a wiped film evaporator, and substantially similar results were obtained.

COMPARATIVE EXAMPLE 1

The same procedures as used in Example 1 were repeated except that a glass-made vacuum jacketed Oldershaw type plate column (40 mm in diameter), which has an actual plate number of 30, which has nearly the same number of the theoretical plates (10.5 plates measured by the total reflux test) as in Example 1 was used.

Although a pressure of 8 Torr was maintained at the top of the distillation column as well as in Example 1, a pressure of more than 60 Torr (a liquid temperature in the evaporator of more than 200° C. based on a presumption) was observed at the bottom in a yield of approximately 85% (a distillation velocity of approximately 155 g/hour) because of large pressure loss through the distillation column.

The distillate remarkably colored (APHA of more than 500).

It is noted that the pressure loss per one theoretical plate was more than 5 Torr [(60–8)/10.5=5] with a yield of approximately 85%.

The result obtained in the comparative Example 1 shows that a product undesirably colors in the case of large pressure loss per one theoretical plate, even using a distillation, column having a number of theoretical plates to remove 2-aminopropanediol-1,3.

COMPARATIVE EXAMPLE 2

The same procedures as used in Example 1 were repeated, except that a glass-made vacuum jacketed Oldershaw type column (40 mm in diameter) having the number of actual plates of 3, which has the number of theoretical plates of 1.3, was used.

When the pressure of 8 Torr was maintained at the top of the distillation column, the pressure of 14 Torr was observed at the bottom, and a product was distilled off at a velocity of 176.5 g/hour (corresponding to a product yield of 97%).

It is noted that pressure loss per one theoretical plate was 4.6 Torr [(14–8)/1.3=4.6] with a yield of 97%.

Although the color hue of the product was 20 (APHA), which is preferred, the 2-aminopropanediol-1,3 content was 0.46% by weight (based on the weight of 1-aminopropanediol- 2,3), which is only slightly improved compared with the starting crude solution.

The results obtained in the Comparative Example 2 show that a product does not color in the case of low pressure loss all over through a distillation column and a distillation under low temperature conditions in an evaporator.

However, the results further teach that the required number of theoretical plates all over through a column to remove 2-aminopropanediol-1,3 can not be attained. As a result, 2-aminopropanediol-1,3 in the product can not be reduced to less than 0.30% (based on the weight of 1-aminopropanediol-2,3).

EXAMPLE 2

The same procedures as used in Example 1 were repeated except that a height of the stacked packing was changed to 660 mm.

When a pressure of 8 Torr was maintained at the top of the distillation column, a pressure of 15 Torr was observed at the bottom, and a product was distilled off at a velocity of 175.2 g/hour (corresponding to a product yield of 96%).

It is noted that a pressure loss per one theoretical plate was 0.3 Torr [(15–8)/21.5=0.3] with a yield of 96%.

A color hue of the product was 30 (APHA), the 2-aminopanediol- 1,3 content was 0.01% (based on the weight of 1-aminopropanediol-2,3).

It is noted that a falling film evaporator equipped with a jacket (heating by steam) made by a stainless steel was also used in place of the wiped film evaporator to give similar results.

COMPARATIVE EXAMPLE 3

The same tests as carried out in Example 1 were repeated, except that a condenser was equipped in an inner part of the evaporator and the column filled with a stacked packing was took off.

It is noted reflux does not occur, because 1-aminopropanediol- 2,3 evaporated is directly condensed in the internal condenser.

As a result, the color hue of the product was 20 (APHA), the 2-aminopanediol-1,3 content was 0.47% (based on the weight of 1-aminopropanediol-2,3) with a yield of 97%.

COMPARATIVE EXAMPLE 4

The same tests as carried out in Comparative Example 3 were repeated, except that the product having 2-aminopropanediol-1,3 content of 0.47% (based on the weight of 1-aminopropanediol-2,3) obtained in Comparative Example 3 was used as a starting material.

It is noted that this test is a repeated purification test of the product obtained in Comparative Example 3.

As a result, although the color hue of the product was also 20 (APHA) with a yield of 96%, the 2-aminopanediol-1,3 content was 0.44% (based on the weight of 1-aminopropanediol-2,3).

Furthermore, it is noted that the 2-aminopanediol-1,3 content of a product was only reduced to 0.37% (based on the weight of 1-aminopropanediol-2,3) in spite of decreasing to a yield of 83%.

EXAMPLE 3

The same tests as carried out in Example 1 were repeated except that the product obtained in Comparative Example 3, which has the 2-aminopanediol-1,3 content of 0.47% (based on the weight of 1-aminopropanediol-2,3), was used as a starting material to obtain a product.

As a result, a color hue of the product was 20 (APHA) in a yield of 96%, the 2-aminopanediol-1,3 content was 0.16% (based on the weight of 1-aminopropanediol-2,3).

Furthermore, it is noted that the 2-aminopanediol-1,3 content of a product surprisingly was reduced to 0.05% (based on the weight of 1-aminopropanediol-2,3) in the case of a yield of 85%.

The test conditions and the results obtained in the above Examples and Comparative Examples are summarized in Table 1 and Table 2.

TABLE 1

|  | Example 1 | Comparative 1 | Example 2 | Example 2 |
|---|---|---|---|---|
| Column | SZ | OS | OS | SZ |
| Number of theoretical plates | 11.4 | 10.5 | 1.3 | 21.5 |
| Pressure at the top of the column (Torr) | 8 | 8 | 8 | 8 |
| Pressure at the bottom of the column (Torr) | 12.5 | 60< | 14 | 15 |
| Yield of a product (%) | 97 | 85 | 97 | 96 |
| 2-APD content in the product (%) | 0.20 | — | 0.46 | 0.01 |
| Color hue of the product (APHA) | 20 | 500< | 20 | 30 |

TABLE 2

|  | Comparative Example 3 | Comparative Example 4 | Example 3 |
|---|---|---|---|
| Column | none | none | SZ |
| Number of theoretical plates | (0.5) | (0.5) | 11.4 |
| Pressure at the top of the column (Torr) | 8 | 8 | 8 |
| Pressure at the bottom of the column (Torr) | (8) | (8) | 12.5 |
| Yield of a product (%) | 97 | 96 | 96 |
| 2-APD content in the product (%) | 0.47 | 0.44 | 0.16 |
| Color hue of the product (APHA) | 20 | 20 | 20 |
| Yield (%) |  | 83 | 85 |
| 2-APD (%) in the product |  | 0.37 | 0.05 |

Note: In Examples 1, 2 and Comparative Examples 1 to 3, the material charged was a crude 1-APD having 2-APD content of 0.50% (based on the weight of 1-APD).

In Example 3 and Comparative Example 4, the material charged was the product obtained in Comparative Example 3.

: 1-APD represents 1-aminopropanediol-2,3
: 2-APD represents 2-aminopropanediol-1,3
: SZ represents Sulzer Packing (a stacked packing)
: OS represents Oldershaw (a conventional plate column)

While the invention has been described in detail and with reference to specific embodiments thereof, it will be apparent to one skilled in the art that various changes and modifications can be made therein without departing from a spirit and scope thereof.

What is claimed is:

1. A process for the preparation of a highly purified 1-aminopropanediol-2,3, comprising distilling a crude 1-aminopropanediol-1,3 containing at least 0.30% of 2-aminopropanediol-1,3 based on the weight of 1-aminopropanediol-2,3 in a temperature range of from 80° to 200° C. and a pressure range of from 0.1 to 30 Torr using a distillation column, said distillation column having a pressure loss of not more than 0.5 Torr per one theoretical plate such that highly purified 1-aminopropanediol-2,3 containing less than 0.30% by weight of 2-aminopropanediol-1,3 is obtained.

2. A process as set forth in claim 1, wherein said distillation column is a packed column.

3. A process as set forth in claim 1, wherein said distillation column is a packed column filled with stacked packings.

4. A process as set forth in claim 1, wherein said distillation column is a packed column filled with Sulzer Packing.

5. A process as set forth in claim 1, wherein distillation is conducted such that the total number of theoretical plates is in a range of from 3 to 100.

6. A process as set forth in claim 1, wherein distillation is conducted such that the total number of theoretical plates is in a range of from 5 to 30.

7. A process as set forth in claim 1, wherein distillation is provided for by use of a liquid-film evaporator.

8. A process as set forth in claim 1, wherein distillation is provided for by use of a wiped-film evaporator.

9. A process as set forth in claim 1, wherein a purity of 1-aminopropanediol-2,3 in said crude 1-aminopropanediol-2,3 is not less than 95%.

10. A process as set forth in claim 1, wherein said crude 1-aminopropanediol-2,3 is prepared by a reaction of ammonia with glycidol or glycerine-alpha-monochlorohydrin.

11. A process as set forth in claim 10, wherein said ammonia is liquid ammonia.

12. A process as set forth in claim 10, wherein said ammonia is an aqueous ammonia.

* * * * *